United States Patent
Tadros et al.

(10) Patent No.: US 6,649,190 B1
(45) Date of Patent: Nov. 18, 2003

(54) GEL FORMULATION

(75) Inventors: Tharwat Fouad Tadros, Wokingham (GB); Philip Taylor, Maidenhead (GB)

(73) Assignee: Syngenta Limited (GB)

(*) Notice: Subject to any disclaimer, the term of this patent is extended or adjusted under 35 U.S.C. 154(b) by 1638 days.

(21) Appl. No.: 08/898,627

(22) Filed: Jul. 22, 1997

Related U.S. Application Data

(63) Continuation of application No. 08/508,018, filed on Jul. 27, 1995, now abandoned.

(30) Foreign Application Priority Data

Jul. 28, 1994 (GB) ............................................... 9415290

(51) Int. Cl.[7] ................................................. A01N 25/04
(52) U.S. Cl. ...................................... 424/487; 424/405
(58) Field of Search .......................... 514/772; 424/487, 424/405, 409

(56) References Cited

U.S. PATENT DOCUMENTS

| | | | | |
|---|---|---|---|---|
| 3,090,736 A | * | 5/1963 | Bashaw et al. | |
| 4,906,276 A | | 3/1990 | Hughes | .......................... 71/77 |
| 5,098,717 A | | 3/1992 | Blackman | ................... 514/648 |
| 5,143,536 A | | 9/1992 | Runkis | .......................... 71/77 |
| 5,185,024 A | * | 2/1993 | Siemer et al. | |
| 5,341,932 A | * | 8/1994 | Chen et al. | .................. 424/409 |

FOREIGN PATENT DOCUMENTS

| | | |
|---|---|---|
| AU | 66501/74 | 9/1975 |
| DE | 2411727 | 9/1974 |
| EP | 251464 | 1/1988 |
| EP | 430634 | 6/1991 |
| EP | 518689 | 12/1992 |
| GB | 948185 | 1/1964 |
| GB | 970579 | 9/1964 |
| GB | 1047601 | 11/1966 |
| GB | 1395502 | 5/1975 |
| GB | 1430207 | 3/1976 |
| GB | 1506568 | 4/1978 |
| JP | 62/201803 | 9/1987 |
| WO | WO 87/2864 | 5/1987 |
| WO | WO 88/6888 | 9/1988 |
| WO | WO 89/4282 | 5/1989 |
| WO | WO 91/19481 | 12/1991 |
| WO | WO 92/1377 | 2/1992 |
| WO | 93/25474 | 6/1993 |
| WO | 96/02239 | 2/1996 |

OTHER PUBLICATIONS

Ullmann's Encyclopedia of Industrial Chemistry, vol. A21, pp. 143–156 (1992).
Ketz Jr. et al., Rheologica Acta 27, 531 (1988).
Nae et al., Rheologica Acta 31, 351 (1992).
Finch et al. (ed). polyvinyl Alcohol, pp. 39–43 (1973).
B.F. Goodrich brochure "CARBOPOL® Water Soluble Resins".

* cited by examiner

*Primary Examiner*—Edward J. Webman
(74) *Attorney, Agent, or Firm*—Thomas Hamilton

(57) ABSTRACT

A water dispersible gel comprising:
(a) an effective amount of an ionic, water soluble agrochemical;
(b) an effective amount of a cross-linked polyacrylic acid;
(c) water; and,
(d) an amount of a base sufficient to cause a mixture of (a), (b) and (c) to gel.

13 Claims, No Drawings

GEL FORMULATION

This application is a continuation of application Ser. No. 08/508,018, filed Jul. 27, 1995.

The present invention relates to a water dispersible agrochemical gel formulation.

Gels comprising a surfactant, an agrochemical, an acrylic acid polymer or copolymer and water are disclosed in W092/01377.

The present invention provides a water dispersible gel comprising (a) an effective amount of an ionic, water soluble agrochemical, (b) an effective amount of a crosslinked polyacrylic acid, (c) water, and (d) an amount of a base sufficient to cause a mixture of (a), (b) and (c) to gel.

The water dispersible gels of the present invention are suitable for packaging in standard containers or for containment in a water-soluble or water dispersible bag. The gels of the present invention are able to be dispersed in water, and the rate of dispersion depends on the degree agitation the gel water mixture is subjected to and also the amount of water present.

The ionic, water soluble agrochemical, is, for example, a herbicide (such as a paraquat salt (for example paraquat dichloride or paraquat bis(methylsulphate), a diquat salt (for example diquat dibromide or diquat alginate) or glyphosate or a salt or ester thereof (such as glyphosate isopropylammonium, glyphosate sesquisodium or glyphosate trimesium (also known as sulfosate)), an insecticide or a fungicide. It is preferred that the ionic, water soluble agrochemical is paraquat dichloride, diquat dibromide, glyphosate isopropylammonium or glyphosate trimesium (also known as sulfosate).

Crosslinked polyacrylic acids preferably have a molecular weight in the range $5 \times 10^5$ to $5 \times 10^6$, especially in the range $1 \times 10^6$ to $4 \times 10^6$. They are available commercially, for example as CARBOPOLs marketed by B F Goodrich (such as CARBOPOLs 5984, 2984, 940, 5984, 910, 941, 934, 934P or ETD 2050).

Suitable bases include ammonium or alkali metal (such as sodium or potassium) hydroxides, carbonates or bicarbonates (for example sodium hydroxide, sodium carbonate or sodium bicarbonate); or amines of formula $R^1R^2R^3N$ (wherein $R^1$, $R^2$ and $R^3$ are, independently, hydrogen or $C_{1-6}$ alkyl [optionally substituted by $C_{1-6}$ alkoxy, hydroxy, halogen, $C_{1-6}$ haloalkoxy (such as $OCF_3$), $C_{1-6}$ hydroxyalkexy (such as $HOCH_2CH_2O$) or $C_{1-4}$ alkoxy($C_{1-6}$)alkoxy (such as $CH_3O$ $(CH_2)_2O$ or $CH_3O(CH_2)$ $_5O$] such as $HOCH_2CH_2$). It is preferred that $R^1$, $R^2$ and $R^3$ are, independently, $C_{1-6}$ alkyl or $C_{1-6}$ alkyl monosubstituted with hydroxy. An amine of formula $R^1R^2R^3N$ is, for example, triethylamine or triethanolamine.

Alkyl and the alkyl part of alkoxy groups are straight or branched chain and preferably contains from 1 to 4 carbon atoms. It is, for example, methyl, ethyl, n-propyl, iso-propyl, n-butyl or tert-butyl.

In one aspect the present invention provides a water dispersible gel comprising (a) 1–60% (especially 5–60%) by weight of an ionic, water soluble agrochemical, (b) 1–4% by weight of a crosslinked polyacrylic acid, (c) 30–80% by weight of water, and (d) 2–20% by weight of a base.

In another aspect the present invention provides a water dispersible gel comprising (a) 20–60% by weight of an ionic, water soluble agrochemical, (b) 1–4% by weight of a crosslinked polyacrylic acid, (c) 30–80% by weight of water, and (d) 2–20% by weight of a base.

In a further aspect the present invention provides a water dispersible gel comprising (a) 20–60% by weight of an ionic, water soluble agrochemical, (b) 1–4% by weight of a crosslinked polyacrylic acid, (c) 30–80% by weight of water, (d) 2–20% by weight of a base, and (e) 1–40% of an electrolyte.

When a gel of the present invention is going to be held in a water-soluble or water dispersible sachet and when the ionic strength of said gel is low it is preferred that said gel comprises a suitable electrolyte in addition to the ionic agrochemical present. The electrolyte helps to improve the insolubility of the material from which the sachet is made in the gel. (See Polyvinyl Alcohol—Properties and Applications pages 38–43, edited by C. A. Finch, published by J Wiley & Sons in 1973 and EP-A1-0518689.) Suitable electrolytes may, for example, comprise a cation or mixtures of cations selected from the list comprising: ammonium, copper, iron, potassium and sodium; and an anion or mixture of anions selected from the list comprising: sulphate, nitrate, fluoride, chloride, bromide, iodide, acetate, tartrate, ammonium tartrate, benzenesulphonate, benzoate, bicarbonate, carbonate, bisulphate, bisulphite, sulphate, sulphite, borate, borotartrate, bromate, butyrate, chlorate, camphorate, chlorite, cinnamate, citrate, disilicate, dithionate, ethylsulphate, ferricyanide, ferrocyanide, fluorosilicate, formate, glycerophosphate, hydrogenphosphate, hydroxostannate, hypochlorite, hyponitrite, hypophosphite, iodate, isobutyrate, lactate, laurate, metaborate, metasilicate, methionate, methylsulphate, nitrite, oleate, orthophosphate, orthophosphite, orthosilicate, oxalate, perborate, perchlorate, phosphate, polyfluoride, polychloride, polyiodide, polybromide, polysulphide, polysulphate, polysulphite, salicylate, silicate, sorbate, stannate, stearate, succinate or valerate. Preferred electrolytes are ammonium sulphate, sodium sulphate, potassium sulphate, copper sulphate, ammonium nitrate, sodium nitrate, potassium nitrate, sodium chloride or potassium chloride.

It is preferred that sufficient base is added to cause the pH of the water dispersible gel to be in the range 6 to 10, especially 6 to 8. If too much base is added the pH of the mixture will be too high and the gel formed will break down. Thus, in another aspect the present invention provides a water dispersible gel comprising (a) an effective amount of an ionic, water soluble agrochemical, (b) an effective amount of a crosslinked polyacrylic acid, (c) water, and (d) an amount of a base sufficient to cause the pH of the resulting gel to lie in the range 6 to 10 (especially 6 to 8, particularly 6 to 7).

In a further aspect the present invention provides a water dispersible gel which comprises 2–5% by weight of an alkali metal hydroxide, carbonate or bicarbonate.

A Bohlin VOR rheometer may be used to measure the elasticity and viscosity of the gel formulation of the present invention under low shear conditions. Here a sinusoidally varying strain (at a frequency of 1 Hz) is applied to a sample of a formulation maintained at 25° C. The resultant stress, which also varies sinusoidally with time, is observed. The ratio of the maximum stress to the maximum strain is known as the complex modulus (G*). By using the phase shift, δ, between the stress and strain wave forms the complex modulus may be split into two components—the storage (elastic) modulus (G') and the loss (viscous) modulus (G"). The storage and loss moduli are a measure of the energy stored and the energy lost respectively, in an oscillatory cycle. The relative magnitude of the loss and storage moduli (G"/G'=Tan δ) provides information on the elasticity of the gel. The lower the value of Tan δ the greater the degree of gelation. Similarly, gels are characterised by their non-Newtonian flow behaviour, exhibiting, for example, yield values and shear thinning. Yield values can be measured using a Haake Rotovisco RV20 under high shear conditions.

In a still further aspect the present invention provides a water dispersible gel as hereinbefore described having a storage modulus (G') in the range 1–1000 Pa, preferably 20–500 Pa, more preferably in the range 100–200 Pa.

In another aspect the present invention provides a water dispersible gel as hereinbefore described having a tan δ (ratio of loss modulus to storage modulus) of less than 1, preferably less than 0.5, more preferably less than 0.2, especially less than 0.1. (Rheological measurements are carried out at a temperature of 25° C. Oscillation measurements are carried out within the linear viscoelastic region as determined by strain sweep measurements made at a frequency of 1 Hz (6.28 rad/s)).

In another aspect the present invention provides a water dispersible gel comprising 10–20% by weight of a base of formula $R^1R^2R^3N$ (wherein $R^1$, $R^2$ and $R^3$ are as defined above).

In another aspect the present invention provides a water dispersible gel comprising 1.5 to 3, especially 2 to 2.75 by weight of a crosslinked polyacrylic acid.

When the gel of the invention is to be contained in a water soluble or water dispersible sachet it is preferred that a plasticiser is included in the gel. The plasticiser is preferably present in the range 0.1 to 1% (especially 0.3 to 0.75%) by weight. Suitable plasticisers include glycols (for example ethylene glycol), glycerine and dibutylphthalate.

Depending on the nature of the ionic, water soluble agrochemical present, one or more adjuvants or co-formulants (such as a wetter or anti-freezing agent) may also be comprised in the gel of the present invention. Adjuvants include a neutral or anionic surfactant [such as a soap, a salt of an aliphatic monoester of sulphuric acid (for example, sodium lauryl sulphate), a salt of a sulphonated aromatic compound (for example, sodium dodecylbenzenesulphonate, an alkyl glucoside or a poiysaccharide].

In a further aspect the present invention provides a gel of the present invention as defined above which also comprises a chelating or sequestering agent for calcium ions. A suitable chelating or sequestering agent is ethylenediaminetetraacetic acid.

Over and above the components already mentioned, a water dispersible gel of the present invention may also comprise an adhesive, an antifoaming agent, a buffer, a deodorant, a dye, an emetic, a preservative, an odourant, a perfume, a safener, a further solvent, a stabiliser, a synergist, a thickener or a wetting agent.

A gel of the invention can be made simply by initially mixing all the components other than the base, and then adding the base to form the gel. Thus it can be appreciated that a gel of the present invention is made by a pH switching process.

In a further aspect the present invention provides a containerisation system comprising a water soluble or water dispersible bag containing a water dispersible gel of the present invention, provided the gel has sufficient ionic strength.

The water soluble or water dispersible bag can be made from a variety of materials and preferred materials are polyethylene oxide, methyl cellulose or, especially, polyvinylalcohol (PVA). The PVA is generally partially or fully alcoholysed or hydrolysed, for example 40–100%, especially 80–100%, alcoholysed or hydrolysed polyvinylacetate film. It is preferred that the PVA film is a laminate of two or more thicknesses of film, a surface modified film or a co-extruded film (such as is described in WO 94/29188).

In another aspect the containerisation system comprises a bag-in-bag arrangement comprising a water-soluble or water dispersible bag holding a gel of the present invention and a second water-soluble or water dispersible bag also holding a gel of the present invention. This bag-in-bag arrangement can be used, for example, to contain a gel of the present invention comprising an ionic, water soluble agrochemical in the inner bag and a gel of the present invention comprising adjuvant, synergist or penetrating agent in the outer bag.

In a further aspect the containerisation system provides two water-soluble or water dispersible bags joined at a common seal, one containing a gel of the present invention comprising one ionic, water soluble agrochemical, the other bag containing a gel of the present invention comprising a different ionic, water soluble agrochemical.

In a still further aspect the containerisation system comprises a bag-in-bag arrangement comprising a first water-soluble or water dispersible bag holding a gel of the present invention and a second water-soluble or water dispersible bag surrounding the first water-soluble or water dispersible bag. The advantage of this system is that the second bag presents a barrier to any matter leaking from the first bag.

In another aspect the containerisation system comprises a bag-in-bag arrangement comprising a first water-soluble or water dispersible bag holding a gel of the present invention and a second water-soluble or water dispersible bag holding an agrochemical composition (such as a liquid, granule, powder or gel composition comprising a fungicide, herbicide, insecticide, adjuvant, synergist or penetrating agent).

In a further aspect the containerisation system comprises a bag-in-bag arrangement comprising a first water-soluble or water dispersible bag holding an agrochemical composition (such as a liquid, granule, powder or gel composition comprising a fungicide, herbicide, insecticide, adjuvant, synergist or penetrating agent) and a second water-soluble or water dispersible bag holding a gel of the present invention.

In another aspect the containerisation system provides two water-soluble or water dispersible bags joined at a common seal, one containing a gel of the present invention comprising a fungicide, herbicide, insecticide, adjuvant, synergist or penetrating agent the other bag containing an agrochemical composition (such as a liquid, granule, powder or gel composition comprising a fungicide, herbicide, insecticide, adjuvant, synergist or penetrating agent).

The water soluble or water dispersible sachet can be formed and filled using standard techniques (such as thermoforming or vertical form-fill-sealing).

In use the containerisation system can be mixed with water to give a sprayable solution or dispersion of the ionic chemical. The containerisation system is especially useful in agriculture.

The following Examples illustrate the invention. CARBOPOL is a Trade Mark of B F Goodrich.

EXAMPLE 1

A solution of sulfosate in water (61.4% w/w, 34.19g) was added to a 5% (w/w) aqueous solution of CARBOPOL 2984 (35.04 g), and water (0.88 g) and ethylene glycol (0.35 g) were then added. The mixture was then shaken and left on rollers to ensure thorough mixing. Sodium hydroxide (2.48 g) was then added to neutralize the acid and bring the pH of the system up to 6.45. This resulted in the CARBOPOL 2984 swelling.

EXAMPLE 2

A solution of sulfosate in water (61.4% w/w, 34.16 g) was added to a 5% (w/w) aqueous solution of CARBOPOL 2984

(21.00 g), and water (14.89 g) and ethylene glycol (0.36 g) were then added. The mixture was then shaken and left on rollers to ensure thorough mixing. Sodium hydroxide (2.27 g) was then added to neutralize the acid and bring the pH of the system up to 6.65. This resulted in the CARBOPOL 2984 swelling.

EXAMPLE 3

A solution of sulfosate in water (61.4% w/w, 34.17 g) was added to a 6% (w/w) aqueous solution of CARBOPOL 2984 (35.00 g), and water (0.90 g) and ethylene glycol (0.35 g) were then added. The mixture was then shaken and left on rollers to ensure thorough mixing. Sodium hydroxide (2.48 g) was then added to neutralize the acid and bring the pH of the system up to 6.23. This resulted in the CARBOPOL 2984 swelling.

EXAMPLE 4

A solution of sulfosate in water (61.4% w/w, 34.18 g) was added to a 5% (w/w) aqueous solution of CARBOPOL 2984 (24.50 g), and water (11.36 g) and ethylene glycol (0.35 g) were then added. The mixture was then shaken and left on rollers to ensure thorough mixing. Sodium hydroxide (2.28 g) was then added to neutralize the acid and bring the pH of the system up to 6.59. This resulted in the CARBOPOL 2984 swelling.

EXAMPLE 5

A solution of sulfosate in water (61.4% w/w, 34.14 g) was added to a 5% (w/w) aqueous solution of CARBOPOL 2984 (31.49 g), and water (4.37 g) and ethylene glycol (0.38 g) were then added. The mixture was then shaken and left on rollers to ensure thorough mixing. Sodium hydroxide (2.39 g) was then added to neutralize the acid and bring the pH of the system up to 6.35. This resulted in the CARBOPOL 2984 swelling.

EXAMPLE 6

A solution of sulfosate in water (61.4% w/w, 39.81 g) was added to a 5% (w/w) aqueous solution of CARBOPOL 2984 (17.51 g), and water (12.77 g) and ethylene glycol (0.35 g) were then added. The mixture was then shaken and left on rollers to ensure thorough mixing. Sodium hydroxide (2.70 g) was then added to neutralize the acid and bring the pH of the system up to 6.52. This resulted in the CARBOPOL 2984 swelling.

EXAMPLE 7

A solution of sulfosate in water (61.4% w/w, 39.81 g) was added to a 5% (w/w) aqueous solution of CARBOPOL 2984 (20.42 g), and water (9.93 g) and ethylene glycol (0.35 g) were then added. The mixture was then shaken and left on rollers to ensure thorough mixing. Sodium hydroxide (2.80 g) was then added to neutralize the acid and bring the pH of the system up to 6.48. This resulted in the CARBOPOL 2984 swelling.

EXAMPLE 8

A solution of sulfosate in water (61.4% w/w, 39.80 g) was added to a 5% (w/w) aqueous solution of CARBOPOL 2984 (23.34 g), and water (6.95 g) and ethylene glycol (0.35 g) were then added. The mixture was then shaken and left on rollers to ensure thorough mixing. Sodium hydroxide (2.88 g) was then added to neutralize the acid and bring the pH of the system up to 6.48. This resulted in the CARBOPOL 2984 swelling.

EXAMPLE 9

A solution of sulfosate in water (61.4% w/w, 39.89 g) was added to a 5% (w/w) aqueous solution of CARBOPOL 2984 (26.23 g), and water (4.09 g) and ethylene glycol (0.36 g) were then added. The mixture was then shaken and left on rollers to ensure thorough mixing. Sodium hydroxide (2.81 g) was then added to neutralize the acid and bring the pH of the system up to 6.38. This resulted in the CARBOPOL 2984 swelling.

EXAMPLE 10

A solution of sulfosate in water (61.4% w/w, 39.78 g) was added to a 5% (w/w) aqueous. solution of CARBOPOL 2984 (29.17 g), and water (1.10 g) and ethylene glycol (0.36 g) were then added. The mixture was then shaken and left on rollers to ensure thorough mixing. Sodium hydroxide (2.85 g) was then added to neutralize the acid and bring the pH of the system up to 6.36. This resulted in the CARBOPOL 2984 swelling.

EXAMPLE 11

A solution of sulfosate in water (61.4% w/w, 39.81 g) was added to a 5% (w/w) aqueous solution of CARBOPOL 2984 (24.63 g), and water (5.82 g) and ethylene glycol (0.35 g) were then added. The mixture was then shaken and left on rollers to ensure thorough mixing. Sodium hydroxide (2.82 g) was then added to neutralize the acid and bring the pH of the system up to 6.23. This resulted in the CARBOPOL 2984 swelling.

EXAMPLE 12

A solution of sulfosate in water (61.4% w/w, 39.79 g) was added to a 5% (w/w) aqueous solution of CARBOPOL 2984 (22.56 g), and water (7.79 g) and ethylene glycol (0.35 g) were then added. The mixture was then shaken and left on rollers to ensure thorough mixing. Sodium hydroxide (2.82 g) was then added to neutralize the acid and bring the pH of the system up to 6.23. This resulted in the CARBOPOL 2984 swelling.

EXAMPLE 13

CARBOPOL 2984 (2.12 g) was mixed with a solution of sulfosate in water (61.4% w/w, 45.50 g) after which and water (12.34 g) and ethylene glycol (0.34 g) were added. The mixture was shaken and left on rollers to ensure thorough mixing. Triethanolamine (10.01 g) was then added to neutralize the acid and bring the pH of the system up to 6.66. This resulted in the CARBOPOL 2984 swelling.

EXAMPLE 14

CARBOPOL 2984 (1.94 g) was mixed with a solution of sulfosate in water (61.4% w/w, 45.51 g) after which water (12.57 g) and ethylene glycol (0.35 g) were added. The mixture was shaken and left on rollers to ensure thorough mixing. Triethanolamine (10.01 g) was added to neutralize the acid and bring the pH of the system up to 6.71. This resulted in the CARBOPOL 2984 swelling.

EXAMPLE 15

CARBOPOL 2984 (1.75 g) was mixed with a solution of sulfosate in water (61.4% w/w, 45.58 g) after which water (12.89 g) and ethylene glycol (0.35 g) were added. The mixture was shaken and left on rollers to ensure thorough mixing. Triethanolamine (10.05 g) were added to neutralize the acid and bring the pH of the system up to 6.81. This resulted in the CARBOPOL 2984 swelling.

EXAMPLE 16

CARBOPOL 2984 (1.41 g) was mixed with a solution of sulfosate in water (61.4% w/w, 45.53 g) after which water (13.12 g) and ethylene glycol (0.35 g) were added. The mixture was shaken and left on rollers to ensure thorough mixing. Triethanolamine (10.05 g) was added to neutralize the acid and bring the pH of the system up to 6.81. This resulted in the CARBOPOL 2984 swelling.

EXAMPLE 17

CARBOPOL 2984 (1.58 g) was mixed with a solution of sulfosate in water (61.4% w/w, 45.55 g) after which water (13.07 g) and ethylene glycol (0.34 g) were added. The mixture was shaken and left on rollers to ensure thorough mixing. Triethanolamine (10.05 g) was added to neutralize the acid and bring the pH of the system up to 6.78. This resulted in the CARBOPOL 2984 swelling.

EXAMPLE 18

CARBOPOL 2984 (1.23 g) was mixed with a solution of sulfosate in water (61.4% w/w, 45.67 g) after which water (13.22 g) and ethylene glycol (0.36 g) were added. The mixture was shaken and left on rollers to ensure thorough mixing. Triethanolamine (10.08 g) was added to neutralize the acid and bring the pH of the system up to 6.87. This resulted in the CARBOPOL 2984 swelling.

EXAMPLE 19

CARBOPOL 2984 (1.05 g) was mixed with a solution of sulfosate in water (61.4% w/w, 45.62 g) after which water (13.43 g) and ethylene glycol (0.37 g) were added. The mixture was shaken and left on rollers to ensure thorough mixing. Triethanolamine (10.13 g) was added to neutralize the acid and bring the pH of the system up to 6.93. This resulted in the CARBOPOL 2984 swelling.

EXAMPLE 20

A solution of sulfosate in water (61.4% w/w, 40.02 g) was added to a 6% (w/w) aqueous solution of CARBOPOL 2984 (26.23 g), and water (20.00 g) was then added. The mixture was then shaken and left on rollers to ensure thorough mixing. Sodium hydroxide (2.77 g) was then added to neutralize the acid and bring the pH of the system up to 6.49. This resulted in the CARBOPOL 2984 swelling.

EXAMPLE 21

A solution of sulfosate in water (61.4% w/w, 40.02 g) was added to a 6% (w/w) aqueous solution of CARBOPOL 2984 (26.67 g), and water (13.33 g) was then added. The mixture was then shaken and left on rollers to ensure thorough mixing. Sodium hydroxide (2.99 g) was then added to neutralize the acid and bring the pH of the system up to 6.47. This resulted in the CARBOPOL 2984 swelling.

EXAMPLE 22

A solution of sulfosate in water (61.4% w/w, 40.07 g) was added to a 6% (w/w) aqueous solution of CARBOPOL 2984 (30.00 g), and water (10.00 g) was then added. The mixture was then shaken and left on rollers to ensure thorough mixing. Sodium hydroxide (2.97 g) was then added to neutralize the acid and bring the pH of the system up to 6.40. This resulted in the CARBOPOL 2984 swelling.

EXAMPLE 23

A solution of sulfosate in water (61.4% w/w, 40.02 g) was added to a 6% (w/w) aqueous solution of CARBOPOL 2984 (33.34 g), and water (6.68 g) was then added. The mixture was then shaken and left on rollers to ensure thorough mixing. Sodium hydroxide (3.59 g) was then added to neutralize the acid and bring the pH of the system up to 6.86. This resulted in the CARBOPOL 2984 swelling.

EXAMPLE 24

A solution of sulfosate in water (61.4% w/w, 250.14 g) was added to a mixture of a 4.7% (w/w) aqueous solution of CARBOPOL 2984 (33.34 g) and ethylene glycol (1.27 g). The mixture was then shaken and left on rollers to ensure thorough mixing. Sodium hydroxide (15.51 g) was then added to neutralize the acid and bring the pH of the system up to 6.28. This resulted in the CARBOPOL 2984 swelling.

A sample of the gel formed (25 g) was placed into a sachet made of polyvinylalcohol (Chris Craft M7030) and the sachet's opening was heat sealed. After storage at 25° C. for 3 months the sachet remained supple and, when put in contact with water, the sachet and its contents readily dispersed.

EXAMPLE 25

A solution of sulfosate in water (61.4%, 20.02 g) was added to a 6.25% (w/w) aqueous solution of CARBOPOL 941 (15.02 g) and water (5.00 g). The mixture was then shaken and left on rollers to ensure thorough mixing. Sodium hydroxide (1.68 g) was then added to neutralize the acid and bring the pH up to 6.57. This resulted in the CARBOPOL 941 swelling.

EXAMPLE 26

A solution of sulfosate in water (61.4%, 20.06 g) was added to a 6.22% (w/w) aqueous solution of CARBOPOL 910 (15.02 g) and water (5.14 g). The mixture was then shaken and left on rollers to ensure thorough mixing. Sodium hydroxide (1.53 g) was then added to neutralize the acid and bring the pH up to 6.44. This resulted in the CARBOPOL 910 swelling.

EXAMPLE 27

A solution of sulfosate in water (61.4%, 26.04 g) was added to a 6.18% (w/w) aqueous solution of CARBOPOL 2984 (30.02 g) and water (24.06 g). The mixture was then shaken and left on rollers to ensure thorough mixing. Sodium hydroxide (3.11g) was then added to neutralize the acid and bring the pH up to 6.72. This resulted in the CARBOPOL 2984 swelling.

EXAMPLE 28

A solution of sulfosate in water (61.4%, 32.50 g) was added to a 6.17% (w/w) aqueous solution of CARBOPOL 2984 (30.00 g) and water (17.52 g). The mixture was then shaken and left on rollers to ensure thorough mixing. Sodium hydroxide (3.01g) was then added to neutralize the acid and bring the pH up to 6.57. This resulted in the CARBOPOL 2984 swelling.

EXAMPLE 29

A solution of sulfosate in water (61.4%, 45.55 g) was added to a 6.17% (w/w) aqueous solution of CARBOPOL 2984 (30.00 g) and water (4.50 g). The mixture was then shaken and left on rollers to ensure thorough mixing. Sodium hydroxide (3.16 g) was then added to neutralize the acid and bring the pH up to 6.51. This resulted in the CARBOPOL 2984 swelling.

EXAMPLE 30

A solution of sulfosate in water (61.4%, 40.09 g) was added to a 5.99% (w/w) aqueous solution of CARBOPOL 2984 (30.00 g) and water (10.00 g). The mixture was then shaken and left on rollers to ensure thorough mixing. Sodium bicarbonate (6.45 g) was then added to neutralize the acid and bring the pH up to 6.66. This resulted in the CARBOPOL 2984 swelling.

EXAMPLE 31

A solution of sulfosate in water (61.4%, 39.99 g) was added to a 6.18% (w/w) aqueous solution of CARBOPOL 2984 (30.009) and water (10.02 g). The mixture was then shaken and left on rollers to ensure thorough mixing. Sodium carbonate (4.80 g) was then added to neutralize the acid and bring the pH up to 6.59. This resulted in the CARBOPOL 2984 swelling.

EXAMPLE 32

A solution of sulfosate in water (61.4%, 40.00 g) was added to a 6.15% (w/w) aqueous solution of CARBOPOL 5984 (30.00 g) and water (10.50 g). The mixture was then shaken and left on rollers to ensure thorough mixing. Sodium hydroxide (3.03 g) was then added to neutralize the acid and bring the pH up to 6.55. This resulted in the CARBOPOL 5984 swelling.

EXAMPLE 33

A solution of sulfosate in water (61.4%, 20.00 g) was added to a 6.19% (w/w) aqueous solution of CARBOPOL ETD 2050 (16.68 g) and water (3.44 g). The mixture was then shaken and left on rollers to ensure thorough mixing. Sodium hydroxide (1.71 g) was then added to neutralize the acid and bring the pH up to 6.71. This resulted in the CARBOPOL ETD 2050 swelling.

EXAMPLE 34

A solution of glyphosate isopropylammonium in water (61.5%, 20.21 g) was added to a (w/w) aqueous solution of 6.17% CARBOPOL 2984 (15.00 g) and water (5.01 g). The mixture was then shaken and left on rollers to ensure thorough mixing. Sodium hydroxide (2.86 g) was then added to neutralize the acid and bring the pH up to 6.49. This resulted in the CARBOPOL 2984 swelling.

EXAMPLE 35

A solution of diquat dibromide in water (26.3% w/v, 32.50 g) was added to a 6.09% (w/w) aqueous solution of CARBOPOL 2984 (11.67 g) and water (8.35 g). The mixture was then shaken and left on rollers to ensure thorough mixing. Sodium hydroxide (0.30 g) and a 40% aqueous solution of sodium hydroxide in water (0.14 g) were then added to neutralize the acid and bring the pH up to 6.42. This resulted in the CARBOPOL 2984 swelling.

EXAMPLE 36

A solution of paraquat dichloride in water (32.3% w/w, 20.01 g) was added to a 6.10% (w/w) aqueous solution of CARBOPOL 2984 (11.68 g) and water (8.45 g). The mixture was then shaken and left on rollers to ensure thorough mixing. Sodium hydroxide (0.24 g) and a 40% aqueous solution of sodium hydroxide (0.16 g) were then added to neutralize the acid and bring the pH up to 6.57. This resulted in the CARBOPOL 2984 swelling.

EXAMPLE 37

A solution of paraquat dichloride in water (32.3% w/w, 25.01 g) was added to a 6.10% (w/w) aqueous solution of CARBOPOL 2984 (15.00 g). The mixture was then shaken and left on rollers to ensure thorough mixing. Sodium hydroxide (0.37 g) and a 40% aqueous solution of sodium hydroxide (0.10 g) were then added to neutralize the acid. This resulted in the CARBOPOL 2984 swelling.

EXAMPLE 38

A solution of paraquat dichloride in water (32.3% w/w, 20.02 g) was added to a 6.13% (w/w) aqueous solution of CARBOPOL 2984 (17.50 g), sodium chloride (1.00 g) and water (2.38 g). The mixture was then shaken and left on rollers to ensure thorough mixing. Sodium hydroxide (0.45 g) was then added to neutralize the acid. This resulted in the CARBOPOL 2984 swelling.

EXAMPLE 39

A solution of sulfosate in water (61.4%, 20.05 g) was added to a 6.10% (w/w) aqueous solution of CARBOPOL 2984 (15.03 g) and water (1.02 g). The mixture was then shaken and left on rollers to ensure thorough mixing. Tri-ethylamine (4.04 g) was then added to neutralize the acid and raise the pH up to 7.29. This resulted in the CARBOPOL 2984 swelling.

EXAMPLE 40

A solution of sulfosate in water (57.6%.w/w, 30.41 g) was added to a 6.55% (w/w) aqueous solution of CARBOPOL 2984 (22.03 g), and water (6.57 g) and ethylenediaminetet-raacetic acid (1.51 g) were then added. The mixture was then shaken and left on rollers to ensure thorough mixing. Sodium hydroxide (2.29 g) was then added to bring the pH of the system up to 6.16. This resulted in the CARBOPOL 2984 swelling.

EXAMPLE 41

A solution of sulfosate in water (57.6% w/w, 30.35 g) was added to a 6.55% (w/w) aqueous solution of CARBOPOL 2984 (21.97 g), and water (5.03 g) and ethylenediaminetet-raacetic acid (3.05 g) were then added. The mixture, was then shaken and left on rollers to ensure thorough mixing. Sodium hydroxide (3.05 g) was then added to bring the pH of the system up to 6.29. This resulted in the CARBOPOL 2984 swelling.

EXAMPLE 42

The rheological properties of the products of the foregoing Examples were measured on a Bohlin rheometer using a cup and bob or cone and plate geometry. The measurements were primarily carried out at a temperature of 25° C. Oscillation measurements were carried out within the linear viscoelastic region as determined by strain sweep measurements made at a frequency of 1 Hz (6.28 rad/s).

The values for the moduli at 1 Hz are presented in TABLE I, where $G^*$ is the complex modulus; $G'$ the storage modulus; $G''$ the loss modulus; $\delta$ the phase angle between the loss and storage moduli; and tan $\delta$ is $G''/G'$.

TABLE I

| EXAMPLE No | $G^*$ (Pa) | $G'$ (Pa) | $G''$ (Pa) | tan $\delta$ |
|---|---|---|---|---|
| 1 | 282 | 281 | 16.4 | 0.058 |
| 2 | 37.3 | 37.2 | 2.95 | 0.079 |
| 3 | 390 | 389 | 20.6 | 0.053 |
| 4 | 72.6 | 72.4 | 4.67 | 0.065 |
| 5 | 215 | 215 | 11.9 | 0.055 |
| 6 | 28.0 | 27.9 | 2.47 | 0.088 |
| 7 | 60.9 | 60.8 | 4.44 | 0.073 |
| 8 | 112 | 112 | 5.90 | 0.053 |
| 9 | 167 | 167 | 8.34 | 0.050 |
| 10 | 255 | 254 | 13.2 | 0.052 |
| 11 | 424 | 423 | 28.1 | 0.066 |
| 12 | 343 | 343 | 19.2 | 0.056 |
| 13 | 407 | 404 | 43.5 | 0.107 |
| 14 | 458 | 452 | 74.8 | 0.165 |
| 15 | 378 | 373 | 62.2 | 0.167 |
| 16 | 125 | 123 | 21.9 | 0.178 |
| 17 | 199 | 196 | 35.2 | 0.179 |
| 18 | 63.0 | 60.9 | 16.1 | 0.264 |
| 19 | 23.3 | 21.9 | 8.12 | 0.37 |
| 20 | 35.8 | 35.6 | 3.58 | 0.10 |
| 21 | 130 | 130 | 8.07 | 0.062 |
| 22 | 154 | 154 | 10.0 | 0.065 |
| 23 | 241 | 240 | 15.4 | 0.061 |
| 24 | 189 | 188 | 11.0 | 0.058 |
| 25 | 88.8 | 86.7 | 19.4 | 0.224 |
| 26 | 53.8 | 50.0 | 19.8 | 0.400 |
| 27 | 359 | 359 | 16.5 | 0.046 |
| 28 | 212 | 212 | 9.69 | 0.046 |
| 29 | 172 | 172 | 8.58 | 0.050 |
| 30 | 204 | 204 | 9.38 | 0.046 |
| 31 | 216 | 215 | 10.8 | 0.050 |
| 32 | 205 | 205 | 13.8 | 0.067 |
| 33 | 279 | 272 | 59.5 | 0.219 |
| 34 | 132 | 130 | 18.3 | 0.141 |
| 35 | 242 | 242 | 10.7 | 0.044 |
| 36 | 201 | 200 | 10.2 | 0.051 |
| 37 | 212 | 211 | 14.2 | 0.067 |
| 38 | 158 | 158 | 8.95 | 0.057 |
| 39 | 223 | 222 | 18.2 | 0.082 |
| 40 | — | 129 | 9.55 | 0.074 |
| 41 | — | 117 | 9.97 | 0.085 |

What is claimed is:

1. A containerization system comprising a water dispersible gel contained in a water-soluble or water dispersible bag; the water dispersible gel comprising:
   (a) 1–60% by weight of an ionic, water-soluble agrocherical;
   (b) 1–4% by weight of a crosslinked polyacrylic acid;
   (c) 30–80% by weight of water; and,
   (d) 2–20% by weight of a base;
   the water dispersible gel having a storage modulus (G') in the range 20–500 Pa and a Tan $\delta$ of less than 0.5.

2. A containerization system as claimed in claim 1, wherein the pH of the gel is in the rang 6 to 10.

3. A containerization system as claimed in claim 1 wherein the crosslinked polyacrylic acid has a molecular weight in the range $5 \times 10^5$ to $5 \times 10^6$.

4. A containerization system as claimed in claim 1 or 2 wherein the base is an ammonium or alkali metal hydroxide, carbonate or bicarbonate; or an amine of formula $R^1R^2R^3N$ wherein $R^1$, $R^2$ and $R^3$ are, independently, hydrogen or $C_{1-6}$ alkyl, optionally substituted by $C_{1-6}$ alkoxy, hydroxy, halogen, $C_{1-6}$ haloalkoxy, $C_{1-6}$ hydroxyalkoxy or $C_{1-4}$ alkoxy($C_{1-6}$)alkoxy.

5. A containerization system as claimed in claim 1 wherein the ionic, water-soluble agrochemical is a paraquat salt, a diquat salt, or a salt or ester of glyphosate.

6. A containerization system as claimed in claim 5 wherein the ionic, water-soluble agrochemical is paraquat dichloride, diquat dibromide, glyphosate isopropylammonium or glyphosate trimesium.

7. A containerization system comprising a water dispersible gel contained in a water-soluble or water dispersible bag; the water dispersible gel being obtainable by mixing:
   (a) 1–60% by weight of an ionic, water-soluble agrochemical;
   (b) 1–4% by weight of a crosslinked polyacrylic acid;
   (c) 30–80% by weight of water; and, finally,
   (d) 2–20% by weight of a base;
   the water dispersible gel having a storage modulus (G') in the range 20–500 Pa and a Tan $\delta$ of less than 0.5.

8. A containerization system as claimed in claim 7, wherein the pH of the gel is in the range 6 to 10.

9. A containerization system as claimed in claim 7 wherein the crosslinked polyacryl acid has a molecular weight in the range $5 \times 10^5$ to $5 \times 10^6$.

10. A containerization system as claimed in claim 7 or 8 wherein the base is an ammonium or alkali metal hydroxide, carbonate or bicarbonate; or an amine of formula $R^1R^2R^3N$ wherein $R^1$, $R^2$ and $R^3$ are, independently, hydrogen or $C_{1-6}$ alkyl, optionally substituted by $C_{1-6}$ alkoxy, hydroxy, halogen, $C_{1-6}$ haloalkoxy, $C_{1-6}$ hydroxyalkoxy or $C_{1-4}$ alkoxy($C_{1-6}$)alkoxy.

11. A containerization system as claimed in claim 7 wherein the ionic, water-soluble agrochemical is a paraquat salt, a diquat salt, or a salt or ester of glyphosate.

12. A containerization system as claimed in claim 11 wherein the ionic, water-soluble agrochemic is paraquat dichloride, diquat dibromide, glyphosate isopropylammonium or glyphosate trimesium.

13. A containerization system comprising a water dispersible gel cotained in a water-soluble or water-dispersible bag, the water dispersible gel comprising:
   (a) an ionic, water-soluble agrochemical;
   (b) the reaction product of a crosslinked polyacrylic acid and a base; and
   (c) 30–80% by weight of water;
   the water dispersible gel having a storage modulus (G') in the range 20–500 Pa and a Tan $\delta$ of less than 0.5.

* * * * *